(12) United States Patent
Brehm et al.

(10) Patent No.: US 10,675,230 B2
(45) Date of Patent: Jun. 9, 2020

(54) COMPOSITIONS COMPRISING CARBAMATE FUNCTIONALIZED ORGANOPOLYSILOXANES AND CATIONIC SURFACTANTS

(71) Applicant: Wacker Chemie AG, Munich (DE)

(72) Inventors: Christof Brehm, Burghausen (DE); Richard Becker, Ann Arbor, MI (US); Elisabeth Hoelzlwimmer, Simbach (DE); Christine Stalleicher, Burghausen (DE)

(73) Assignee: WACKER CHEMIE AG, Munich (DE)

(*) Notice: Subject to any disclaimer, the term of this patent is extended or adjusted under 35 U.S.C. 154(b) by 39 days.

(21) Appl. No.: 16/096,150

(22) PCT Filed: Apr. 24, 2017

(86) PCT No.: PCT/EP2017/059652
§ 371 (c)(1),
(2) Date: Oct. 24, 2018

(87) PCT Pub. No.: WO2017/186638
PCT Pub. Date: Nov. 2, 2017

(65) Prior Publication Data
US 2019/0133906 A1  May 9, 2019

(30) Foreign Application Priority Data

Apr. 26, 2016 (DE) .................. 10 2016 207 063

(51) Int. Cl.
| | |
|---|---|
| *A61K 8/41* | (2006.01) |
| *C11D 3/00* | (2006.01) |
| *C11D 1/62* | (2006.01) |
| *C11D 3/37* | (2006.01) |
| *A61Q 5/02* | (2006.01) |
| *A61K 8/898* | (2006.01) |
| *A61Q 5/12* | (2006.01) |
| *C11D 11/00* | (2006.01) |
| *A61K 8/891* | (2006.01) |

(52) U.S. Cl.
CPC ............ *A61K 8/416* (2013.01); *A61K 8/898* (2013.01); *A61Q 5/02* (2013.01); *A61Q 5/12* (2013.01); *C11D 1/62* (2013.01); *C11D 3/0015* (2013.01); *C11D 3/3742* (2013.01)

(58) Field of Classification Search
None
See application file for complete search history.

(56) References Cited

U.S. PATENT DOCUMENTS

| | | | |
|---|---|---|---|
| 3,642,858 A | 2/1972 | Frevel et al. | |
| 3,915,867 A | 10/1975 | Kang et al. | |
| 4,137,180 A | 1/1979 | Naik et al. | |
| 5,296,622 A | 3/1994 | Uphues et al. | |
| 5,399,652 A | 3/1995 | Bindl et al. | |
| 6,213,737 B1 | 4/2001 | Murakami et al. | |
| 6,551,986 B1 | 4/2003 | Littig et al. | |
| 6,642,200 B1 | 11/2003 | Zhang et al. | |
| 7,135,451 B2 | 11/2006 | Corona, III et al. | |
| 2008/0307586 A1 | 12/2008 | Hodge et al. | |
| 2011/0104085 A1 | 5/2011 | Klug et al. | |

FOREIGN PATENT DOCUMENTS

| | | |
|---|---|---|
| DE | 1619058 A1 | 1/1971 |
| DE | 1935499 A1 | 1/1971 |
| EP | 0239910 A2 | 10/1987 |
| EP | 0459821 A2 | 12/1991 |
| EP | 0563961 A1 | 10/1993 |
| EP | 0639369 A1 | 2/1995 |
| JP | 2047371 A2 | 2/1990 |
| JP | 11062878 A2 | 3/1999 |
| JP | 2009052155 A2 | 3/2009 |
| JP | 20069052154 A2 | 3/2009 |
| JP | 2010202984 A2 | 9/2010 |
| JP | 2010530036 A | 9/2010 |
| JP | 2011525176 A | 9/2011 |
| WO | 09150213 A1 | 12/2009 |
| WO | 11123727 A2 | 10/2011 |
| WO | 2011123737 A1 | 10/2011 |

OTHER PUBLICATIONS

D. B. Solarek "Modified Starches, Properties and Uses" (CRC Press, 1986), Chapter 8, p. 113-129.
Ullmann's Encyclopedia of Industrial Chemistry, 2003, Wiley-VCH Verlag.
G. Engelhardt, H. Jancke; J. Organometal. Chem. 28 (1971), 293-300.
Chapter 8—NMR spectroscopy of organosilicon compounds, Elizabeth A. Williams, The Chemistry of Organic Silicon Compounds, 1989 John Wiley and Sons Ltd., 511-533.

*Primary Examiner* — Jeffrey T. Palenik
(74) *Attorney, Agent, or Firm* — Brooks Kushman P.C.

(57) ABSTRACT

Emulsions of carbamato-functional organopolysiloxanes emulsified with the aid of cationic emulsifiers are useful for treating textiles to provide good haptic properties, and also in hair care products.

16 Claims, No Drawings

COMPOSITIONS COMPRISING CARBAMATE FUNCTIONALIZED ORGANOPOLYSILOXANES AND CATIONIC SURFACTANTS

CROSS REFERENCE TO RELATED APPLICATIONS

This application is the U.S. National Phase of PCT Appln. No. PCT/EP2017/059652 filed Apr. 24, 2017, which claims priority to German Application No. 10 2016 207 063.0 filed Apr. 26, 2016, the disclosures of which are incorporated in their entirety by reference herein.

BACKGROUND OF THE INVENTION

1. Field of the Invention

The invention relates to compositions comprising carbamato-functionalized organopolysiloxanes and to the use thereof for the treatment of fibers, especially of textile fibers and textile fabrics.

2. Description of the Related Art

Many formulations are used in consumer textile products in order to achieve a particular benefit. Examples are exceptional softness, improved tactile properties or the reduction of wrinkles.

Typically, formulations of this kind comprise water-insoluble, quaternary ammonium compounds having generally at least two long-chain alkyl or alkenyl chains. Owing to their higher biodegradability, there has been increasing interest in those quaternary ammonium compounds that contain long-chain alkyl or alkenyl groups interrupted by functional groups, for example carboxyl groups. Compounds of this kind have long been known and are described, for example, in DE 16 19 058 A1, DE 19 35 499 A1, U.S. Pat. No. 3,915,867 or EP 239 910 A2.

There are also known formulations comprising combinations of emulsifiers, including cationic emulsifiers, and functionalized polydiorganosiloxanes, for example amino-functionalized polydiorganosiloxanes, polydiorganosiloxanes with quaternary functionalizations or hydroxypropylamino-functionalized polydiorganosiloxanes. Formulations of this kind are described, for example, in WO 2011/123727 A2 or WO 2011/123737 A1.

Silicones as constituents of formulations in consumer products have likewise long been known. Silicone-containing formulations comprising carbamato-functionalized polydiorganosiloxanes are described for textile finishing, for example, in JP 2047371 A2. The softness is caused on the part of the textiles by the treatment of nonionically stabilized emulsions of carbamato-functionalized polydiorganosiloxanes. The carbamato-functionalized polydiorganosiloxanes are reaction products from the reaction of amino-modified polydimethylsiloxanes of amine value>0.5 mmol/g and mixtures of ethylene carbonate and propylene carbonate, where more than 50 mol % of the amino groups have been functionalized with carbamato groups. Such a high functionalization of more than 50 mol % of the amino groups is necessary to reduce yellowing of the textile.

WO 2009/150213 A1 describes the use of carbamato-functionalized polydiorganosiloxanes for the finishing of organic fibers and textiles. The carbamato-functionalized polydiorganosiloxanes described in WO 2009/150213 A1 are reaction products of amino-modified polydimethylsiloxanes of amine value>0.5 mmol/g with glycerol carbonate in which all amino groups have been functionalized.

JP 2009-052154, JP 2009-052155 and JP 2010-202984 likewise disclose formations for textile finishing, where carbamato-functionalized polydiorganosiloxanes are used in combination with selected nonionic surfactants. Here too, the carbamato-functionalized polydiorganosiloxanes are based on amino-modified polydimethylsiloxanes of amine value>0.5 mmol/g.

The problem addressed was that of providing compositions which comprise carbamato-functionalized polydiorganosiloxanes and are suitable for treatment, especially for care and cleaning, of fibers such as textiles, wherein the fibers, after treatment thereof, have improved properties such as soft hand, rapid water absorption, low tendency to crease and easy ironing without observation of yellowing. The problem is solved by the invention.

SUMMARY OF THE INVENTION

The invention provides compositions comprising
(A) at least 0.1% by weight and at most 10.0% by weight of carbamato-functionalized organopolysiloxanes containing on average per molecule at least one carbamato-functional Y group of the formula $$—R^4—[NX—R^5—]_n NX—H$$

where
X is the same or different and is a hydrogen atom or a Z radical of the formula $$—CO—O—CHR^6—CH_2—OH \text{ or } —CO—O—CH_2—CHR^6—OH$$

where on average at least one X radical per molecule is a Z radical,
where $R^4$ is the same or different and is a divalent, Si—C-bonded hydrocarbyl radical having 1 to 18 carbon atoms,
$R^5$ is the same or different and is a divalent hydrocarbyl radical having 1 to 6 carbon atoms,
$R^6$ is the same or different and is a hydrogen atom or a monovalent hydrocarbyl radical having 1 to 36 carbon atoms, where one or more —$CH_2$— groups may be replaced by heteroatoms, preferably by —O— or —S—,
n is 1, 2, 3 or 4, preferably 1,
(B) at least 1% by weight and at most 80% by weight of cationic surfactants and
(C) at least 30% by weight and at most 97% by weight of water, based in each case on the total weight of the aqueous compositions.

DETAILED DESCRIPTION OF THE PREFERRED EMBODIMENTS

The compositions of the invention preferably contain at least 0.25% by weight, more preferably at least 0.4% by weight, and preferably at most 5% by weight, more preferably at most 3% by weight, of carbamato-functionalized organopolysiloxanes (A).

The compositions of the invention preferably contain at least 1.5% by weight, more preferably at least 2.5% by weight, and preferably at most 40% by weight, more preferably at most 25% by weight, of cationic surfactants (B).

The compositions of the invention contain preferably at least 45% by weight, more preferably at least 60% by weight, and preferably at most 97% by weight, more preferably at most 95% by weight, of water (C).

Preference is given to using the carbamato-functionalized organopolysiloxanes (A) in the form of aqueous emulsions thereof. The aqueous emulsions of the carbamato-functionalized organopolysiloxanes (A) are stabilized using nonionic emulsifiers and/or cationic emulsifiers and/or protective colloids.

Preference is given especially to the use of nonionic emulsifiers or a combination of nonionic and cationic emulsifiers for stabilization of the emulsions, since they give rise to particularly high compatibility in the composition of the invention.

Carbamato-functionalized polydiorganosiloxanes (A) have long been known and are described, for example, in JP 2047371 A2.

In the compositions of the invention, preference is given to using carbamato-functionalized organopolysiloxanes (A) containing the following structural units:

M $[R^1_2R^2SiO_{1/2}]$ and/or M' $[R^1_2(Y)SiO_{1/2}]$
and
D $[R^1_2SiO_{2/2}]$ and/or D' $[R^2(Y)SiO_{2/2}]$ and/or T' $[(Y)SiO_{3/2}]$
and optionally
T $[R^1SiO_{3/2}]$ and/or
Q $[SiO_{4/2}]$
with the proviso that on average per molecule at least one structural unit having a carbamato-functional group Y is present and where on average per molecule at least one Y group contains a Z radical,
where
$R^1$ is the same or different and is a monovalent Si—C-bonded hydrocarbyl radical having 1 to 18 carbon atoms,
$R^2$ is the same or different and is an $R^1$ radical or a hydroxyl group —OH or alkoxy group of the formula —O—$R^3$ where $R^3$ is an optionally substituted alkyl radical having 1-8 carbon atoms, and Y is as defined above.

In the compositions of the invention, preference is given to using carbamato-functionalized polydiorganosiloxanes (A) of the following formula:

$$[R^1_2R^2SiO_{1/2}]_2[R^2(Y)SiO_{2/2}]_k[R^1_2SiO_{2/2}]_m \quad (I)$$

where
$R^1$, $R^2$ and Y are as defined above, where on average per molecule at least one Y group contains a Z radical,
m is an integer and is at least 40, preferably at least 65, more preferably at least 110, and at most 1000, preferably at most 800, more preferably at most 500,
k is an integer and is at least 1, preferably at least 2, and at most 40, preferably at most 20, more preferably at most 10, where the ratio of m to k is at least 25, preferably at least 40, more preferably at least 70, and at most 1000, preferably at most 500, more preferably at most 150.

In the carbamato-functionalized organopolysiloxanes (A), especially carbamato-functionalized polydiorganosiloxanes (A), preferably at least 5 mol %, more preferably at least 15 mol %, especially at least 20 mol %, and preferably less than 50 mol %, more preferably less than 40 mol %, especially less than 30 mol %, of the N-bonded X radicals in the Y groups are not a hydrogen atom, but are Z radicals.

This means that preferably at least 5 mol % and preferably less than 50 mol % of the amino groups have been functionalized by Z radicals, i.e. carbamato groups.

It is optionally also possible for small amounts of structural units T or Q to be present in the carbamato-functionalized polydiorganosiloxanes (A) of the formula (I).

The carbamato-functionalized organopolysiloxanes (A) used in the composition of the invention are preferably prepared by reaction of amino-functionalized organopolysiloxanes (A') containing on average per molecule at least one group Y' of the formula —$R^4$—[NH—$R^5$-]$_n$NH$_2$ where $R^4$, $R^5$ and n are as defined above
with cyclic carbonates.

For preparation of the carbamato-functionalized organopolysiloxanes (A), preference is given to using amino-functionalized polydiorganosiloxanes (A') of the following formula:

$$[R^1_2R^2SiO_{1/2}]_2[R^2(Y')SiO_{2/2}]_k[R^1_2SiO_{2/2}]_m \quad (I')$$

where
$R^1$, $R^2$, m, and k are as defined above,
Y' is a group of the general formula —$R^4$—[NH—$R^5$—]$_n$NH$_2$ where $R^4$, $R^5$ and n are as defined above.

Cyclic carbonates used are preferably those of the following formula:

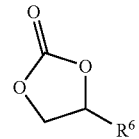

where
$R^6$ is as defined above.

For preparation of the carbamato-functionalized organopolysiloxanes (A), the amount of cyclic carbonate used is selected such that, in the carbamato-functionalized organopolysiloxane (A) prepared, preferably at least 5 mol %, more preferably at least 15 mol %, especially at least 20 mol %, and preferably less than 50 mol %, more preferably less than 40 mol %, especially less than 30 mol %, of the N-bonded X radicals in the Y groups are converted to Z radicals.

Examples of hydrocarbyl radicals $R^1$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical; cycloalkyl radicals such as cyclopentyl, cyclohexyl, cycloheptyl and methylcyclohexyl radicals.

Preferred examples of $R^1$ are the methyl, ethyl, octyl and dodecyl radicals. A particularly preferred example of $R^1$ is the methyl radical.

Examples of hydrocarbyl radicals $R^2$ are the radicals as described for the $R^1$ radical or a hydroxyl group —OH or an alkoxy group of the formula —O—$R^3$ where $R^3$ is a methyl, ethyl, n-propyl, isopropyl, 1-n-butyl, 2-n-butyl, isobutyl, tert-butyl, n-pentyl, isopentyl, neopentyl, or tert-pentyl radical, hexyl radicals such as the n-hexyl radical, heptyl radicals such as the n-heptyl radical, octyl radicals such as the n-octyl radical and isooctyl radicals such as the 2,2,4-trimethylpentyl radical.

Preferred examples of $R^2$ are the methyl radical, the ethyl radical, the hydroxyl group, the methoxy radical and the ethoxy radical.

Examples of $R^4$ are divalent hydrocarbyl radicals such as the methylene group, the 1,2-ethylene group, the 1,3-propylene group, the 1,3-butylene group, the 1,4-butylene group, the 1,5-pentylene group, and the 1,6-hexylene group.

Particularly preferred examples are the 1,3-propylene group and the 1,3-butylene group.

Examples of $R^5$ are divalent hydrocarbyl radicals such as the 1,2-ethylene group, the 1,3-propylene group, the 1,3-butylene group, the 1,4-butylene group, the 1,5-pentylene group, and the 1,6-hexylene group.

A particularly preferred example is the 1,2-ethylene group.

$R^6$ is preferably a hydrogen atom or a monovalent hydrocarbyl radical optionally substituted by —O— and having 1 to 10 carbon atoms, preferably having 1 to 6 carbon atoms, more preferably an alkyl or alkoxyalkyl radical having 1 to 10 carbon atoms, especially one having 1 to 6 carbon atoms.

Preferred examples of the Y' radicals are
—(CH$_2$)$_2$NH(CH$_2$)$_2$NH$_2$,
—(CH$_2$)$_3$NH(CH$_2$)$_2$NH$_2$,
—(CH$_2$)$_3$NH(CH$_2$)$_3$NH$_2$,
—(CH$_2$—CH(CH$_3$)—CH$_2$—) NH(CH)$_2$NH$_2$, and
—(CH$_2$)$_4$NH(CH$_2$)$_4$NH$_2$.

Particularly preferred examples of the Y' radicals are
—(CH$_2$)$_3$NH(CH$_2$)$_2$NH$_2$ and
(CH$_2$—CH(CH$_3$)—CH$_2$—) NH(CH)$_2$NH$_2$.

The indices k and m in formula (I') are chosen such that the viscosity of the amino-functionalized polydiorganosiloxanes (A') used is preferably at least 50 mPas, more preferably at least 100 mPas, especially at least 250 mPas, measured in each case at 25° C. and a shear rate of 10/s, and preferably at most 100,000 mPas, more preferably at most 50,000 mPas, especially at most 10,000 mPas, measured in each case at 25° C. and a shear rate of 5/s.

The ratio of k and m is chosen such that the amino-functionalized polydiorganosiloxanes (A') preferably have an amine value of at least 0.1 mmol/g, more preferably at least 0.15 mmol/g, especially at least 0.2 mmol/g, and preferably at most 1.0 mmol/g, more preferably at most 0.7 mmol/g, especially at most 0.4 mmol/g.

The cyclic carbonates used for preparation of the carbamato-functionalized polydiorganosiloxanes (A) are either commercially available or can be synthesized, for example as described in U.S. Pat. No. 3,642,858 A.

Typically, the cyclic carbonates used are 1,2-alkylene carbonates or alkoxyalkyl-substituted ethylene carbonates. Preferred cyclic carbonates are those carbonates where $R^6$ is a hydrogen atom or a monovalent hydrocarbyl radical, optionally substituted by —O— and having 1 to 10 carbon atoms, more preferably having 1 to 6 carbon atoms.

Examples are ethylene carbonate, 1,2-propylene carbonate, 1,2-butylene carbonate, 1,2-pentylene carbonate, 1,2-hexylene carbonate, 1,2-octylene carbonate, 1,2-dodecylene carbonate, 3-methyl-1,2-butylene carbonate, 3-methyl-1,2-pentylene carbonate, 3-ethyl-1,2-pentylene carbonate, 4-methyl-1,2-pentylene carbonate, 5-methyl-1,2-hexylene carbonate, 3-methoxy-1,2-propylene carbonate, 3-ethoxy-1,2-propylene carbonate, 3-n-propoxy-1,2-propylene carbonate, 4-methoxy-1,2-butylene carbonate, 4-ethoxy-1,2-butylene carbonate, S-methoxy-3-butylene carbonate, and 5-methoxy-1,2-heptylene carbonate.

Preferred cyclic carbonates are ethylene carbonate, 1,2-propylene carbonate, and 3-methoxy-1,2-propylene carbonate. A particularly preferred cyclic carbonate is 1,2-propylene carbonate.

The cationic surfactants used in the compositions of the invention are preferably
(B1) quaternary ammonium surfactants of the formula

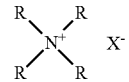

(B1)

where R is independently a hydrogen atom, an alkyl group, an alkenyl group, a hydroxyalkyl group, a benzyl group or a group of the formula —(C$_p$H$_{2p}$O)$_q$—H where p is an integer from 1 to 4 and q is an integer from 2 to 5, and X$^-$ is a halide, a sulfate, a sulfonate, a nitrate, a methylsulfate or an ethylsulfate anion, preferably a chloride or methylsulfate anion,
or
(B2) ester-/amido-containing quaternary ammonium surfactants of the formula

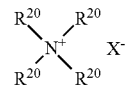

(B2)

where at least one $R^{20}$ radical is a monovalent hydrocarbyl radical containing a G group of the formula —O—(O)C—, —C(O)—O—, —NR—C(O)—, or —C(O)—NR— or —CR=NR,
and the further $R^{20}$ radicals are independently an R group or a radical of the formula —$R^{20'}$—N$^+$R$^{20}_3$ X$^-$
where $R^{20'}$ is an alkylene group,
the two ammonium groups R$^{20}_3$N$^+$X$^-$ are joined to one another to form an R$^{20}_3$N-alkylene-NR$^{20}_3$ 2 X$^-$ compound,
or two $R^{20}$ radicals form an optionally unsaturated ring, and
R and X$^-$ are as defined above.

Preference is given to ester/amido- or imido-containing quaternary ammonium surfactants of the formula (B2).

The cationic surfactants used in the compositions of the invention may be one kind of surfactant or else two or more kinds of surfactants.

The quaternary ammonium surfactants (B1) are (B1-1) surfactants of the formula $$R^{21}R^{22}R^{23}R^{24}N{+}X^-$$ (B1-1)

where
$R^{21}$, $R^{22}$ are independently an alkyl group having 1 to 4 carbon atoms, a hydroxyalkyl group having 1 to 4 carbon atoms, a benzyl group or a group of the formula —(C$_p$H$_{2p}$O)$_q$—H, where p is an integer from 1 to 4 and q is an integer from 2 to 5,
$R^{23}$, $R^{24}$ are independently an alkyl or alkenyl group having 8 to 22 carbon atoms or
$R^{23}$ is an alkyl group having 8 to 22 carbon atoms and
$R^{24}$ is an alkyl group having 1 to 10 carbon atoms, a hydroxyalkyl group having 1 to 10 carbon atoms, a benzyl group or a group of the formula —(C$_p$H$_{2p}$O)$_q$—H where p and q are as defined above, and
X$^-$ is a halide, a sulfate, a sulfonate, a nitrate, a methylsulfate or an ethylsulfate anion, especially a chloride or methylsulfate anion,
or
(B1-2) surfactants of the formula $$R^{25}_{(4-r)}R^{26}_rN^+X^-$$ (B1-2)

where
$R^{25}$ is independently a hydrogen atom, an alkyl group having 1 to 3 carbon atoms, for example the methyl, the ethyl or the propyl group, a hydroxyalkyl group having 1 to 3 carbon atoms, for example the hydroxyethyl group, a benzyl group or a group of the formula —$(C_pH_{2p}O)_q$—H where p is an integer from 1 to 4, preferably 2, and q is an integer from 2 to 5, $R^{26}$ is a hydrocarbyl radical having 12 to 24 carbon atoms, especially an alkyl or alkenyl radical having 12 to 24 carbon atoms, r is 2 or 3, and $X^-$ is as defined above.

The ester/amido-containing quaternary ammonium surfactants (B2) are preferably those selected from the group of (B2-1) surfactants of the formula

(B2-1)

where
$R^{25}$ is independently a hydrogen atom, an alkyl group having 1 to 3 carbon atoms, for example the methyl, the ethyl or the propyl group, a hydroxyalkyl group having 1 to 3 carbon atoms, for example the hydroxyethyl group, a benzyl group or a group of the formula —$(C_pH_{2p}O)_q$—H where p is an integer from 1 to 4, preferably 2, and q is an integer from 2 to 5, $R^{26}$ is a monovalent hydrocarbyl radical, preferably an alkyl or alkenyl radical having 12 to 24 carbon atoms, $R^{27}$ is a divalent linear or branched alkylene radical having 1 to 6 carbon atoms, more preferably having 1 to 3 carbon atoms, especially the ethylene, n-propylene or i-propylene group, $G^1$ is a —O—(O)C—, —C(O)—O—, —NR—C(O)—, or —C(O)NR— group, r is 2 or 3 and $X^-$ is as defined above, (B2-2) surfactants of the formula

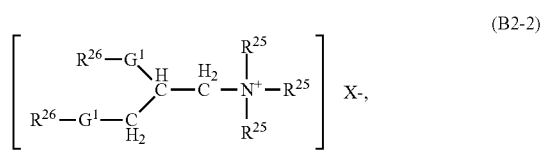

(B2-2)

where
$R^{25}$, $R^{26}$, $G^1$ and $X^-$ are as defined above, especially surfactants of the formula

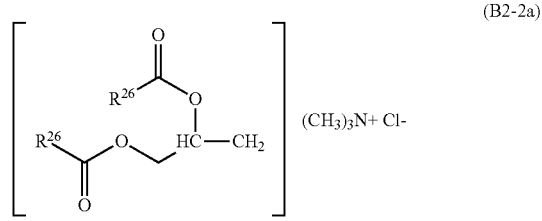

(B2-2a)

where
$R^{26}$ is as defined above, where, in the case that the surfactant (B2-2a) is described as the diester, monoesters may also be present (where surfactants of this kind and general methods for preparation thereof are described in U.S. Pat. No. 4,137,180), (B2-3) surfactants of the formula

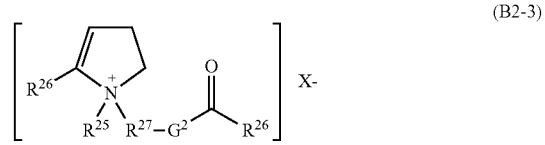

(B2-3)

where
$G^2$ is an oxygen atom or the $NR^{25}$ group,
$R^{25}$, $R^{26}$, $R^{27}$ and X are as defined above, (B2-4) surfactants of the formula

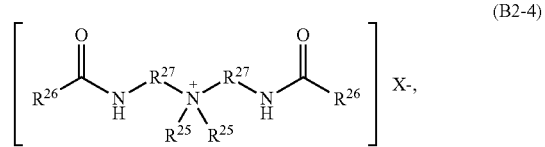

(B2-4)

where
$R^{25}$, $R^{26}$, $R^{27}$ and X are as defined above,
(where quaternary surfactants of this kind are described in U.S. Pat. No. 5,296,622), (B2-5) surfactants of the formula

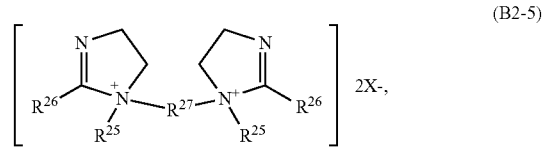

(B2-5)

where
$R^{25}$, $R^{26}$, $R^{27}$ and $X^-$ are as defined above, and mixtures thereof.

Examples of surfactants of the formula (B1-1) are
(a) monoalkyl-quaternary ammonium salts, for example
the behenyltrimethylammonium salt,
the stearyltrimethylammonium salt
the cetyltrimethylammonium salt and
the hydrogenated tall oil alkyltrimethylammonium salt
and
(b) dialkyl-quaternary ammonium salts, for example
dialkyl($C_{14}$-$C_{18}$)dimethylammonium chloride,
ditallowalkyldimethylammonium chloride,
distearyldimethylammonium chloride and
dicetyldimethylammonium chloride.

Examples of surfactants of the formula (B1-2) are dialkyldimethylammonium salts, such as dioleyldimethylammonium chloride (available from Witco Corporation under the Adogen® 472 brand name).

Examples of surfactants of the formula (B2-1) are
N,N-bis(stearoyloxyethyl)-N,N-dimethylammonium chloride,
N,N-bis(talloyloxyethyl)-N,N-dimethylammonium chloride,
N,N-bis(stearoyloxyethyl)-N-(2-hydroxyethyl)-N-methylammonium methylsulfate and N,N-bis[ethyl(tallowate)]-N-(2-hydroxyethyl)-N-methyl-ammoniummethylsulfate.

Surfactants of the formula (B2-2) are abbreviated to DEQ or else are referred to as "propyl" ester quat of the general designation 2,3-di(acyloxy)propyltrimethylammonium chloride. One example of surfactants of the formula (B2-2) is 2,3-di(stearoyloxy)propyltrimethylammonium chloride.

One example of surfactants of the formula (B2-3) is 1-methyl-1-stearoylamidoethyl-2-stearoylimidazolinium methylsulfate (available from Witco Corporation under the Varisoft® brand name).

Examples of surfactants of the formula (B2-4) are difatty acid amidoamine-based products of the formula:

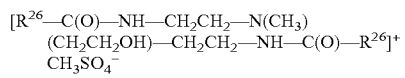

where $R^{26}$ is as defined above,
for example a product available from Witco Corporation under the Varisoft® 222LT brand name.

The compositions of the invention may include, in addition to the carbamato-functionalized polydiorganosiloxanes (A) and cationic surfactants (B), further substances such as perfumes, electrolytes, nonaqueous solvents, deposition auxiliaries, pH regulators, dyes or foam inhibitors.

Examples of further substances are perfumes. Perfumes when present are preferably used in an amount of 0.01% to 3% by weight, more preferably in amounts of 0.1% to 2.5% by weight and especially in amounts of 0.2% to 1.5% by weight, based in each case on the total weight of the compositions of the invention. Perfume oils or fragrances used may be individual odorant compounds, for example the synthetic products of the ester, ether, aldehyde, ketone, alcohol and hydrocarbon type.

However, preference is given to using mixtures of various odorants which together produce a pleasing fragrance note.

Perfume oils of this kind may also comprise natural odorant mixtures as obtainable from plant sources.

Examples of further substances are electrolytes. Electrolytes when present are preferably used in an amount of 0.01% to 5% by weight, based on the total weight of the compositions of the invention. Electrolytes used from the group of the inorganic salts may be a wide range of very different salts. Preferred cations are the alkali metals and alkaline earth metals; preferred anions are the halides and sulfates. From a preparation point of view, preference is given to the use of NaCl or $MgCl_2$ in the compositions of the invention.

Examples of further substances are nonaqueous solvents. Nonaqueous solvents when present are preferably used in an amount of 0.25% to 15% by weight, more preferably 0.25% to 12% by weight, especially 0.25% to 9% by weight, based in each case on the total weight of the compositions of the invention.

The nonaqueous solvents that may be used in the compositions of the invention come, for example, from the group of the mono- or polyhydric alcohols, alkanolamines or glycol ethers, provided that they are miscible with water within the concentration range specified. The solvents are preferably selected from ethanol, n- or i-propanol, butanols, glycol, propane- or butanediol, glycerol, diglycol, propyl- or butyldiglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, methoxytriglycol, ethoxytriglycol, butoxytriglycol, dipropylene glycol monomethyl ether, dipropylene glycol monoethyl ether, 1-butoxyethoxy-2-propanol; 3-methyl-3-methoxybutanol, propylene glycol t-butyl ether and mixtures of these solvents.

Examples of further substances are deposition auxiliaries. Deposition auxiliaries when present are preferably used in an amount of 0.01% by weight to 10% by weight, more preferably of 0.05% by weight to 5% by weight, especially of 0.15% by weight to 3% by weight, based in each case on the total weight of the compositions of the invention.

Suitable deposition auxiliaries are described, for example, in U.S. patent application Ser. No. 12/080,358.

The deposition auxiliaries may be both cationic and amphoteric polymers.

Cationic polymers and processes for preparation thereof are known in general terms in the literature. The cationic polymer may have a cationic charge density of about 0.005 to about 23 meq./g, more preferably of about 0.01 to about 12 meq./g, especially preferably of about 0.1 to about 7 meq./g at a given pH of the composition. In the case of amine-containing polymers, the charge density depends on the pH of the compositions, and therefore the charge density is measured at the intended pH of the product.

Corresponding pH values are generally within a range from about 2 to about 11, especially from about 2.5 to about 9.5. The charge density is calculated by dividing the number of net charges per repeat unit by the molecular weight of the repeat unit. The positive charges may be present on the backbone of the polymers and/or on the side chains of the polymers.

Examples of deposition auxiliaries are cationic or amphoteric polysaccharides, proteins and synthetic polymers. Cationic polysaccharides may include cationic cellulose derivatives, cationic guar gum derivatives, chitosan and derivatives thereof, and cationic starches.

Cationic polysaccharides have a molecular weight of about 50,000 to about 3,500,000. Suitable cationic polysaccharides include cationic cellulose ethers, especially cationic hydroxyethyl cellulose and cationic hydroxypropyl cellulose. Examples of cationic hydroxyalkyl cellulose are (INCI name) Polyquaternium 10 (available, for example, under the Ucare™ Polymer JR 30M, JR 400, JR 125, LR 400 and LK 400 trade names from Amerchol Corp.), Polyquaternium 67 (available, for example, under the Softcat SK™ trade name from Amerchol Corp.) and Polyquaternium 4 (available, for example, under the trade names Celquat™ H200 and Celquat L-200™ from national Starch and Chemical Company).

Further suitable polysaccharides are hydroxyethyl cellulose or hydroxypropyl cellulose that have been quaternized with glycidyl-$C_{12}$-$C_{22}$-alkyldimethylammonium chloride. One example of these is (INCI name) Polyquaternium 24 (available, for example, under the Quaternium LM 200 trade name from Amerchol Corp.). Cationic guar gum derivatives include cationically derivatized galactomannans or cationic carob seed flour. One example of a cationic guar gum is the quaternary ammonium derivative of hydroxypropyl guar, available, for example, under the Jaguar® C13 or Jaguar® Excel trade name (from Rhodia) or N-Hance® trade name (from Aqualon).

Cationic starches have been described, for example, by D. B. Solarek in "Modified Starches, Properties and Uses" (CRC Press, 1986) and in U.S. Pat. No. 7,135,451.

A further group of suitable cationic polymers includes those that are prepared by polymerization of ethylenically unsaturated monomers with a suitable initiator or catalyst (described by way of example in U.S. Pat. No. 6,642,200).

Suitable polymers from this group are polyethyleneimines and derivatives thereof or synthetic polymers that are prepared by polymerization of one or more cationic monomers.

Monomers of this kind may be N,N-dialkylaminoalkyl acrylate, N,N-dialkylaminoalkyl methacrylate, N,N-dialkylaminoalkyl-acrylamide, N,N-dialkylaminoalkylmethacrylamide, quaternized N,N-dialkylaminoalkyl acrylate, quaternized N,N-dialkylaminoalkyl methacrylate, quaternized N,N-dialkylaminoalkylacryl-amide, quaternized N,N-dialkylaminoalkylmethacrylamide, methacrylamidopropyl-pentamethyl-1,3-propylen-2-olammonium dichloride, N,N,N,N',N',N'',N''-heptamethyl-N''-3-(1-oxo-2-methyl-2-propenyl)aminopropyl-9-oxo-8-azo-decane-1,4,10-triammonium trichloride, vinylamine and derivatives thereof, allylamine and derivatives thereof, vinylimidazole, quaternized vinylimidazole or diallyldialkylammonium chloride and combinations thereof, and optionally a second monomer selected from the group consisting of acrylamide, N,N-dialkylacrylamide, methacrylamide, N,N-dialkylmethacrylamide, $C_1$-$C_{12}$-alkyl acrylate, $C_1$-$C_{12}$-hydroxyalkyl acrylate, polyalkylene glycol acrylate, $C_1$-$C_{12}$-alkyl methacrylate, $C_1$-$C_{12}$ hydroxyalkyl methacrylate, polyalkylene glycol, vinyl acetate, vinyl alcohol, vinylformamide, vinylacetamide, vinyl alkyl ethers, vinylpyridine, vinylpyrrolidone, vinylimidazole, vinylcaprolactam and derivatives, acrylic acid, methacrylic acid, maleic acid, vinylsulfonic acid, styrenesulfonic acid, acrylamidopropylmethanesulfonic acid (AMPS) and salts thereof. Through use of branching and crosslinking monomers, the polymer may optionally be branched or crosslinked. Branching and crosslinking monomers may be: ethylene glycol diacrylate, divinylbenzene and butadiene. In addition, the composition may comprise amphoteric deposition auxiliaries, provided that the polymer has a positive net charge. Polymers of this kind have a cationic charge density of about 0.05 to about 18 meq./g.

Examples of suitable cationic polymers from this group are poly(acrylamide-co-diallyldimethylammonium chloride), poly(acrylamidomethacrylamidopropyltrimethylammonium chloride), poly(acrylamido-co-N,N-dimethylaminoethyl acrylate) and quaternized derivatives thereof, poly(acrylamide-co-N,N-dimethylaminoethyl methacrylate) and quaternized derivatives thereof, poly(hydroxyethyl acrylate-co-dimethylaminoethyl methacrylate), poly(hydroxypropyl acrylate-co-dimethylaminoethyl methacrylate), poly(co-hydroxypropyl acrylate-methacrylamidopropyltrimethylammonium chloride), poly(acrylamide-co-diallyldimethylammonium chloride-co-acrylic acid), poly(acrylamide-methacrylamidopropyltrimethylammonium chloride-co-acrylic acid), poly(diallyldimethylammonium chloride), poly(vinylpyrrolidone-co-dimethylaminoethyl methacrylate), poly(ethyl methacrylate-co-quaternized dimethylaminoethyl methacrylate), poly(ethyl methacrylate-co-oleyl methacrylate-co-diethylaminoethyl methacrylate), poly(diallyldimethyl-ammonium chloride-co-acrylic acid), poly(vinylpyrrolidone-co-quaternized vinylimidazole) and poly(acrylamide-co-methacrylamidopropylpentamethyl-1,3-propylen-2-olammonium chloride).

Suitable deposition auxiliaries include Polyquaternium-1, Polyquaternium-5, Polyquaternium-6, Polyquaternium-7, Polyquaternium-8, Polyquaternium-11, Polyquaternium-14, Polyquaternium-22, Polyquaternium-28, Polyquaternium-30, Polyquaternium-32 and Polyquaternium-33 (INCI names).

Another group of suitable cationic polymers may be that of alkylamine-epichlorohydrin polymers. These are reaction products of amines and oligoamines with epichlorohydrin, as described, for example, in U.S. Pat. Nos. 6,642,200 and 6,551,986.

Examples include dimethylamine-epichlorohydrin-ethylenediamine, available under the Cartafix® CB and Cartafix® TSF trade name (from Clariant).

A further group of suitable synthetic cationic polymers includes polyamidoamine-epichlorohydrin resins (PAE resins).

The most common PAE resins are the condensation products of diethylenetriamine with adipic acid, which are then reacted with epichlorohydrin. Resins of this kind are available, for example, under the Kymene™ brand name (from Hercules Inc.) or Luresin™ brand name (from BASF). The cationic polymers may contain charge-neutralizing anions, such that the overall polymer is neutral under ambient conditions. Examples of suitable counterions (in addition to anions that form during use) include chloride, bromide, sulfate, methylsulfate, sulfonate, methylsulfonate, carbonate, bicarbonate, formate, acetate, citrate, nitrate and mixtures thereof.

The weight-average molecular weight of any polymer used as deposition agent may be from about 500 daltons to about 5,000,000 daltons, more preferably from about 1000 daltons to about 2,000,000 daltons, especially from about 2500 daltons to about 1,500,000 daltons measured by size exclusion chromatography relative to polyethylene oxides as standard via RI detection. The molecular weight of the cationic polymer may most preferably be from about 500 daltons to about 37,500 daltons.

Examples of further substances are pH regulators. pH regulators can be used in such an amount in the compositions of the invention that the pH of the compositions of the invention is preferably between 1 and 8, more preferably between 1 and 6 and especially between 1.5 and 3.5. It is possible here to use all known acids and alkalis, provided that their use is not forbidden for application-related or environmental reasons or for reasons of consumer protection.

Examples of further substances are dyes, in order to improve the esthetic impression of the compositions of the invention.

Preferred dyes, the selection of which presents no difficulty at all to one skilled in the art, have high storage stability and insensitivity to the other ingredients of the compositions of the invention and to light.

Examples of further substances are foam inhibitors, for example soaps, paraffins or silicone oils, which may optionally have been applied to support materials.

Examples of further substances are small amounts of nonionic surfactants in order, for example, to ensure homogeneous dispersion of the perfume oil.

For production of the compositions of the invention, the cationic surfactant (B) is generally first melted and the melt is dispersed in water. Subsequently, the carbamato-functionalized polydiorganosiloxane (A) in an aqueous emulsion and optionally the further ingredients, for example the electrolyte, the defoamer and the dye, are mixed in. Finally, if appropriate, the perfume is added.

The carbamato-functionalized polydiorganosiloxane (A) in an aqueous emulsion may also be initially charged and optionally be diluted with water, in order to subsequently disperse the molten cationic surfactant (B) therein.

The carbamato-functionalized polydiorganosiloxanes (A) are preferably used in the form of their aqueous emulsions. In the aqueous emulsions, the carbamato-functionalized polydiorganosiloxanes (A) are preferably used in amounts of at least 5% by weight, more preferably at least 7% by weight, especially at least 10% by weight, and preferably at most 70% by weight, more preferably at most 50% by weight, especially at most 40% by weight, based in each case on the total weight of the emulsions.

The aqueous emulsions of the carbamato-functionalized polydiorganosiloxanes (A) are stabilized using emulsifiers (E); these may be nonionic emulsifiers and/or cationic emulsifiers and/or protective colloids, especially nonionic emulsifiers or a combination of nonionic and cationic emulsifiers.

Examples of Nonionic Emulsifiers are:
1. Polyvinyl alcohol still having 5% to 50%, preferably 8% to 20%, vinyl acetate units, having a degree of polymerization of 500 to 3000.
2. Alkyl polyglycol ethers, preferably those having 3 to 40 EO units and alkyl radicals of 8 to 20 carbon atoms.
3. Alkylaryl polyglycol ethers, preferably those having 5 to 40 EO units and 8 to 20 carbon atoms in the alkyl and aryl radicals.
4. Ethylene oxide/propylene oxide (EO/PO) block copolymers, preferably those having 8 to 40 EO/PO units.
5. Addition products of alkylamines with alkyl radicals of 8 to 22 carbon atoms with ethylene oxide or propylene oxide.
6. Fatty acids having 6 to 24 carbon atoms.
7. Alkyl polyglycosides of the general formula R*—O—$Z_o$ in which R* is a linear or branched, saturated or unsaturated alkyl radical having an average of 8-24 carbon atoms and $Z_o$ is an oligoglycoside radical having an average of o=1-10 hexose or pentose units or mixtures thereof.
8. Natural substances and derivatives thereof, such as lecithin, lanolin, saponins, cellulose; cellulose alkyl ethers and carboxyalkyl celluloses, the alkyl groups of which each have up to 4 carbon atoms.
9. Linear organo(poly)siloxanes containing polar groups, especially containing the elements O, N, C, S, P, Si, especially those having alkoxy groups having up to 24 carbon atoms and/or up to 40 EO and/or PO groups.

Examples of cationic emulsifiers are:
10. Salts of primary, secondary and tertiary fatty amines having 8 to 24 carbon atoms with acetic acid, sulfuric acid, hydrochloric acid and phosphoric acids.
11. Alkylpyridinium, alkylimidazolinium and alkyloxazolinium salts, especially those wherein the alkyl chain has up to 18 carbon atoms, especially the halides, sulfates, phosphates and acetates.
12. Cationic surfactants of the formula (B1) (quaternary ammonium surfactants) and of the formula (B2) (ester/amido-containing quaternary ammonium surfactants), as described above.

Particularly suitable ampholytic emulsifiers are:
13. Amino acids having long-chain substitution, such as N-alkyldi(aminoethyl)glycine or N-alkyl-2-aminopropionic salts.
14. Betaines such as N-(3-acylamidopropyl)-N,N-dimethylammonium salts having a $C_8$-$C_{18}$-acyl radical and alkylimidazolium betaines.

Preferred emulsifiers are nonionic emulsifiers, especially the alkyl polyglycol ethers listed above under 2, and cationic emulsifiers, especially the cationic surfactants listed above under 12. The emulsifiers (E) may be used alone or in the form of a mixture of two or more abovementioned emulsifiers; they may be used in pure form or as solutions of one or more emulsifiers in water or organic solvents.

In the aqueous emulsions of the inventive carbamato-functionalized polydiorganosiloxanes (A), the emulsifiers (E) are preferably used in amounts of at least 1% by weight, more preferably at least 2% by weight, especially at least 3% by weight, and preferably at most 25% by weight, more preferably at most 20% by weight, especially at most 15% by weight, based in each case on the total weight of the emulsions.

In addition, to reduce the particle size and to decrease the amount of emulsifiers (E) required in the aqueous emulsions of the carbamato-functionalized polydiorganosiloxanes (A), it is possible to use cosurfactants (Co-E).

Cosurfactants (Co-E) are understood to mean polar compounds of moderate molar mass, such as alcohols of molecule size $C_3$ to $C_8$, suitable di- and polyols, amines, esters and ketones.

These come from the group, for example, of the mono- or polyhydric alcohols, alkanolamines or glycol ethers, provided that they are miscible with water within the concentration range specified. The solvents are preferably selected from ethanol, n- or i-propanol, butanols such as 1-butanol, 2-butanol or 2-methyl-2-propanol, pentanols such as 1-pentanol, 2-pentanol or 3-pentanol, hexanols such as 1-hexanol, 2-hexanol or 3-hexanol, heptanols such as 1-heptanol, 2-heptanol, 3-heptanol or 4-heptanol, octanols such as 1-octanol, 2-octanol, 3-octanol or 4-octanol, glycol, propanediol, butanediols such as butane-1,2-diol or butane-1,3-diol, hexanediols such as hexane-1,2-diol or 2-methylpentane-2,4-diol, octanediols such as 2-ethylhexane-1,3-diol or octane-1,2-diol, glycerol, diglycol, propyl- or butyldiglycol, ethylene glycol methyl ether, ethylene glycol ethyl ether, ethylene glycol propyl ether, ethylene glycol mono-n-butyl ether, diethylene glycol methyl ether, diethylene glycol ethyl ether, diethylene glycol mono-n-butyl ether, propylene glycol methyl ether, propylene glycol ethyl ether, propylene glycol propyl ether, propylene glycol n-butyl ether, propylene glycol tert-butyl ether, methoxytriglycol, ethoxytriglycol, butoxytriglycol, dipropylene glycol monomethyl ether, dipropylene glycol monoethyl ether, 1-butoxyethoxy-2-propanol or 3-methyl-3-methoxybutanol, 1-aminobutane, 2-aminobutane, 2-amino-2-methylpropane, 1-aminopentane, 2-aminopentane, 1-aminohexane, 1-aminoheptane and 1-aminooctane; ethyl acetate, propyl acetate, isopropyl acetate, butyl acetate, isobutyl acetate, pentyl acetate, isopentyl acetate and hexyl acetate; methyl propionate, ethyl propionate and tert-butyl propionate; methyl butyrate, ethyl butyrate, propyl butyrate and butyl butyrate; 2-butanone, 2-pentanone, 3-pentanone, 4-methyl-2-pentanone, 2-hexanone, 3-hexanone, 2-heptanone, 3-heptanone, 4-heptanone, 5-methyl-3-heptanone, 2-octanone and 3-octanone and mixtures of these cosurfactants.

Examples of preferred cosurfactants (Co-E) are 1-alkanols from the above-adduced examples having $C_5$ to $C_8$ chains, alkanediols from the above-adduced examples having $C_4$ to $C_8$ chains, glycerol, propyl acetate, butyl acetate and pentyl acetate, 2-pentanone and the above-adduced ethylene glycol, propylene glycol, dipropylene glycol or diethylene glycol monoalkyl ethers.

In the inventive aqueous emulsion of the carbamato-functionalized polydiorganosiloxanes (A), the coemulsifiers (Co-E), when used, are preferably used in amounts of at least 1% by weight, more preferably at least 2% by weight, especially at least 3% by weight, and preferably at most 15% by weight, more preferably at most 10% by weight, especially at most 7% by weight, based in each case on the total weight of the emulsions.

The inventive aqueous emulsions of the carbamato-functionalized polydiorganosiloxanes (A) may comprise acids (F) for establishment of a desired pH or for formation of acid addition salts with the amino-containing radicals (Y) of the carbamato-functionalized polydiorganosiloxanes (A).

Examples of mineral acids which can be reacted with the aforementioned amino-containing radicals (Y), for example, are hydrochloric acid, perchloric acid, sulfuric acid, sulfurous acid, nitric acid, nitrous acid, hydrofluoric acid, phosphoric acids, diphosphoric acids and polyphosphoric acids. Examples of suitable carboxylic acids are formic acid, acetic acid, propionic acid, butanoic acids, citric acid, trichloric acetic acid, dichloric acetic acid and chloroacetic acid, trifluoroacetic acid, cyanoacetic acid, phenylacetic acid, benzoic acid, m- and p-nitrobenzoic acid, oxalic acid, malonic acid and lactic acid.

Particular preference is given to acetic acid and formic acid.

The inventive aqueous emulsions of the carbamato-functionalized polydiorganosiloxanes (A) may, as well as emulsifier (E), optionally cosurfactant (Co-E) and optionally acid (F), also comprise additives (H). Examples of additives (H) are especially bactericides, fungicides, algicides, microbicides, fragrances, corrosion inhibitors, dyes, pigments, thickeners and fillers.

The emulsifying operation for production of the inventive aqueous emulsion of the carbamato-functionalized polydiorganosiloxanes (A) is preferably conducted at temperatures of at least 10° C., more preferably at least 15° C. and preferably at most 80° C., more preferably at most 70° C.

The increase in temperature preferably comes about through the introduction of mechanical shear energy which is required for the emulsification process. The increase in temperature is not required to accelerate any chemical process. Moreover, the process of the invention is preferably conducted at the pressure of the surrounding atmosphere, but can also be conducted at higher or lower pressures.

The inventive emulsions of the carbamato-functionalized polydiorganosiloxanes (A) are produced by vigorous commixing of the carbamato-functionalized polydiorganosiloxane (A) in aqueous medium with the emulsifier (E), optionally the coemulsifier (Co-E), optionally acids (F) and optionally additives (H). Stable emulsions are formed. As a result, the carbamato-functionalized polydiorganosiloxanes (A) are in finely divided form.

The inventive emulsions of the carbamato-functionalized polydiorganosiloxanes (A) may be produced batchwise or continuously.

Technologies for production of emulsions of organopolysiloxanes are known. Thus, the vigorous mixing and dispersing can be effected in rotor-stator stirrer apparatuses, colloid mills, high-pressure homogenizers, microchannels, membranes, jet nozzles and the like, or by means of ultrasound. Homogenizing equipment and processes are described, for example, in Ullmann's Encyclopedia of Industrial Chemistry, CD-ROM edition 2003, Wiley-VCH Verlag, under "Emulsions".

The way in which the components that are used for production of the emulsions of the invention are mixed is not very critical and can be executed in varying sequence. Depending on the components (A), (E), optionally (Co-E), optionally (F) and optionally (H), however, preferred procedures may arise and should be examined in the individual case.

For example, the initial charge may comprise component (A) and optionally the acid (F), then the emulsifiers (E) and optionally the coemulsifiers (Co-E) are added and then the dispersant and optionally additives (H) are incorporated. In many cases, it has been found that it is advantageous to include the emulsifiers (E), optionally coemulsifiers (Co-E) and optionally acid (F) together with a portion of the dispersant water in the initial charge in the emulsification apparatus, and to incorporate component (A) and the further components into this mixture obtained.

In the process of the invention, the dispersant water is used in amounts of preferably at least 1% by weight, more preferably at least 5% by weight, especially at least 10% by weight, and preferably at most 99% by weight, more preferably at most 95% by weight, especially at most 90% by weight, based in each case on the total weight of all ingredients of the emulsion.

The compositions of the invention composed of carbamato-functionalized polydiorganosiloxanes (A) and cationic surfactants (B) find use as active ingredient compositions in products for care and cleaning.

The term "active ingredient" here is understood to mean a substance which fulfills the purpose of (a) providing care for an article, i.e. keeping an article in its original form, reducing or preventing the effects of outside influences (e.g. time, light, temperature, pressure, soiling, chemical reaction with other reactive compounds that come into contact with the article), for example aging, soiling, material fatigue, bleaching, or even improving desired positive properties of the article, and (b) cleaning an article, i.e. bringing about or assisting the removal of impurities as a result of the use of the article.

If the care for an article comprises the treatment of textile fibers or fabrics, it is possible to use the compositions of the invention to achieve, for example, the following advantageous effects:

Achievement of a distinct improvement in softness of the fibers/fabric after washing, reduction in crease formation in the fabric during the rinsing and drying stages, reduction in the occurrence of folds or creases prior to ironing, decrease in the force required to iron the fabric, protection from formation of creases during use, retention of the shape of the textile fabric in the course of washing, care and use, improvement in the wettability of the fibers/fabric, reduction in the effect of pilling (i.e. of pill or fuzz formation) in textile fabrics, suppression of the effect of dry rigidity that occurs in drying laundry, achievement of greater elasticity in fibers/fabrics, achievement of improved gloss in fibers, or reduction in fading of colors in fibers/fabrics.

In this connection, products for care and cleaning are understood to mean the following compositions or formulations:

formulations used in the household and industry for care and cleaning of surfaces, for example fibers, leather, cloth, wood, glass, ceramic, tiles, linoleum, plastic. Examples of products for cleaning and care of such surfaces are laundry detergents (heavy duty laundry detergents, color laundry detergents, fabric softeners etc.), dishwashing detergents, machine dishwashing detergents, rinse aids, neutral detergents, window-cleaning products, all-purpose cleaners, glass cleaners, sanitary cleaners, toilet cleaners, carpet cleaners, car care products.

Formulations used for treatment of keratinic fibers such as hair. Preference is given to using the cosmetic compositions for washing and care of hair. Examples of products for washing and care of hair are hair shampoos, rinse-off conditioners, hair tonics, hair masks, hair serums, hair foams, hairstyling sprays, hair creams, hair gels, hair oils, hair tip fluids and hair colorants.

The invention therefore provides washing and cleaning compositions, especially fabric softeners, comprising the compositions of the invention.

The compositions of the invention may either be used directly as washing and cleaning compositions, especially fabric softeners, or are present in the washing and cleaning compositions, especially fabric softeners, preferably in amounts of 10% to 90% by weight.

The invention therefore provides a method of care and cleaning of fibers, especially textile fibers and textile fabrics, with the compositions of the invention or with the washing and cleaning compositions comprising the compositions of the invention.

The invention further provides cosmetic formulations, especially hair treatment compositions, comprising the compositions of the invention.

The compositions of the invention may either be used directly in cosmetic formulations, especially hair treatment compositions, or are present in cosmetic formulations, especially hair treatment products, in amounts of preferably 10% to 90% by weight.

The invention therefore provides a method of care and washing of hair with the compositions of the invention or with the cosmetic formulations comprising the compositions of the invention.

In the examples which follow, all figures for parts and percentages, unless stated otherwise, are based on weight.

Unless stated otherwise, the examples which follow are conducted at a pressure of the surrounding atmosphere, i.e. at about 1000 hPa, and at room temperature, i.e. about 20° C., or a temperature which is established on combination of the reactants at room temperature without additional heating or cooling.

The viscosities were measured on an "MCR 302" rheometer from Anton Paar according to DIN EN ISO 3219: 1994 and DIN 53019, using a cone-plate system (CP50-2 cone) with an opening angle of 2°. The instrument was calibrated with 10000 standard oil from the Physikalisch-Technischen Bundesanstalt [German National Metrology Institute]. The measurement temperature is 25.00° C.+/−0.05° C., the measurement time 3 min. The viscosity figure is the arithmetic mean of three independently conducted individual measurements. The measurement uncertainty of the dynamic viscosity is 1.5%. The shear rate gradient was chosen as a function of the viscosity and is given separately for each viscosity figure.

The amine value states how many mmol of KOH are equivalent to 1 g of the substance to be determined. The amine value is determined according to DIN 16945-Version 1989-03.

$^1$H NMR spectra are recorded as a solution in $CDCl_3$ on a Bruker Avance 500 NMR spectrometer (5 mm selective 1H NMR sample head) with a measurement frequency of 500.13 MHz.

The evaluation is effected as known to the person skilled in the art and described in the following literature: "Über die $^1$H—, $^{13}$C— and $^{29}$Si-NMR chemischen Verschiebungen einiger linearer, verzweigter and cyclischer Methyl-Siloxan-Verbindungen" [On the $^1$H, $^{13}$C and $^{29}$Si Chemical Shifts of Some Linear, Branched and Cyclic Methylsiloxane Compounds], G. Engelhardt, H. Jancke; J. Organometal. Chem. 28 (1971), 293-300; "Chapter 8—NMR spectroscopy of organosilicon compounds", Elizabeth A. Williams, The Chemistry of Organic Silicon Compounds, 1989 John Wiley and Sons Ltd, 511-533.

The particle sizes were determined on a Zetasizer Nano-S particle sizer, from Malvern, Software Version 6.01, by means of dynamic light scattering (Mie analysis method). For this purpose, the emulsions were diluted to 0.5% by weight with filtered and degassed water. The values reported are always based on the D(50) value. D(50) should be considered to be the volume-averaged particle diameter at which 50% of all the particles measured have a volume-average diameter smaller than the D(50) value given.

EXAMPLES

Example 1: Carbamato-Functionalized Polydimethylsiloxane 1

300.0 g of a mixedly hydroxy/methoxy-terminated copolymer composed of aminoethylaminopropylmethylsiloxane and dimethylsiloxane units, of viscosity 1057 mPas (at 25° C. and at a shear rate of 10 l/s) and of amine value 0.295 mmol/g, are initially charged in a 500 mL three-neck flask under a nitrogen atmosphere, and 4.52 g of propylene carbonate are added. The reaction mixture is gradually heated up to 50° C. and stirred at this temperature for two hours. After cooling, a clear product 1 of viscosity 3173 mPas (at 25° C. and at a shear rate of 10 l/s) is obtained. The $^1$H NMR spectrum shows a degree of functionalization with respect to carbamate of 46% of all amino groups available.

Example 2: Carbamato-Functionalized Polydimethylsiloxane 2

715.6 g of a mixedly hydroxy/methoxy-terminated copolymer composed of aminoethylaminopropylmethylsiloxane and dimethylsiloxane units, of viscosity 982 mPas (at 25° C. and at a shear rate of 10 l/s) and of amine value 0.287 mmol/g, are initially charged in a 1000 mL three-neck flask under a nitrogen atmosphere, and 5.00 g of propylene carbonate are added. The reaction mixture is gradually heated up to 50° C. and stirred at this temperature for two hours. After cooling, a clear product 2 of viscosity 2280 mPas (at 25° C. and at a shear rate of 10 l/s) is obtained. The $^1$H NMR spectrum shows a degree of functionalization with respect to carbamate of 23% of all amino groups available.

Example 3: Carbamato-Functionalized Polydimethylsiloxane 3

300.0 g of a trimethylsilyl-terminated copolymer composed of aminoethylaminopropylmethylsiloxane and dimethylsiloxane units, of viscosity 1111 mPas (at 25° C. and at a shear rate of 10 l/s) and of amine value 0.595 mmol/g, and 34.2 g of dipropylene glycol monobutyl ether (commercially available under the DOWANOL® DPnB name from Aldrich) are initially charged in a 500 mL three-neck flask under a nitrogen atmosphere, and 9.20 g of propylene carbonate are added. The reaction mixture is gradually heated up to 50° C. and stirred at this temperature for two hours. After cooling, a clear product 3 of viscosity 1570 mPas (at 25° C. and at a shear rate of 10 l/s) is obtained. The $^1$H NMR spectrum shows a degree of functionalization with respect to carbamate of 48% of all amino groups available.

Example 4: Emulsion E1 of the Carbamato-Functionalized Polydimethylsiloxane 1

An Ultra-Turrax T 50 emulsifying apparatus (from Janke & Kunkel/IKA) is initially charged with 4.0 g of isotridecyl octaethoxylate, commercially available under the Lutensol TO 8 brand name (from BASF), 2.0 g of isotridecyl pentaethoxylate, commercially available under the Lutensol TO 5 brand name (from BASF) and 6.9 g of demineralized water. 33.0 g of the carbamato-functionalized product 1 are added in five portions under a high shear of 6000 to 8000 rpm, so as to result in a relatively firm, stiff phase as the preliminary emulsion. 0.8 g of concentrated acetic acid is added and the emulsion is diluted with 60.2 g of demineralized water in portions with low shear to give the desired emulsion. The result is a milky white emulsion having an average particle size of 61 nm. The emulsion is homogeneous and stable even after storage at room temperature for 6 months.

Example 5: Emulsion E2 of the Carbamato-Functionalized Polydimethylsiloxanes 2

Emulsion E2 is prepared by the same method as described in example 3, but with the carbamato-functionalized polydimethylsiloxanes 2 from example 2. The result is a milky white emulsion having an average particle size of 145 nm. The emulsion is homogeneous and stable even after storage at room temperature for 6 months.

Example 6: Emulsion E3 of the Carbamato-Functionalized Polydimethylsiloxanes 3

Emulsion E3 is prepared by the same method as described in example 4, but with the carbamato-functionalized polydimethylsiloxanes 3 from example 3. The result is a milky white emulsion having an average particle size of 157 nm. The emulsion is homogeneous and stable even after storage at room temperature for 6 months.

Example 7: Microemulsion E4 Formed from Carbamato-Functionalized Polydimethylsiloxane 2

An Ultra-Turrax T 50 emulsifying apparatus (from Janke & Kunkel/IKA) is initially charged with 5.5 g of isotridecyl pentaethoxylate, commercially available under the Lutensol TO 5 brand name (from BASF), 2.50 g of diethylene glycol monobutyl ether, commercially available under the Butyldiglycol trade name (from Brenntag) and 8.0 g of demineralized water. 16.5 g of the carbamato-functionalized product 2 are added in five portions under a high shear of 6000 to 8000 rpm, so as to result in a relatively firm, stiff phase as the preliminary emulsion. 0.1 g of concentrated acetic acid is added and the emulsion is diluted with 75.3 g of demineralized water in portions with low shear to give the desired emulsion. The result is a clear emulsion E4 having an average particle size of 19 nm. The emulsion is homogeneous and stable even after storage at room temperature for 6 months.

Example 8: Cationic Emulsions E5 of Carbamato-Functionalized Polydimethylsiloxane 2

An Ultra-Turrax T 50 emulsifying apparatus (from Janke & Kunkel/IKA) is initially charged with 10.4 g of isotridecyl octaethoxylate, commercially available under the Lutensol TO 8 brand name (from BASF), 5.2 g of isotridecyl pentaethoxylate, commercially available under the Lutensol TO 5 brand name (from BASF), 0.54 g of N,N-bis[ethyl(tallowate)]-N-(2-hydroxyethyl)-N-methylammonium methylsulfate (90% ethanolic solution), commercially available under the Stepantex® VK90 brand name (from Stepan) and 10.7 g of demineralized water. 69.4 g of the carbamato-functionalized product 2 are added in two portions under a high shear of 4000 to 6000 rpm, so as to result in a pasty preliminary emulsion. 0.4 g of concentrated acetic acid is added, and the emulsion is diluted with 102.9 g of demineralized water in portions under low shear to give the desired emulsion. The result is an opalescent emulsion E5 having an average particle size of 90 nm. The emulsion is homogeneous and stable even after storage at room temperature for 6 months.

Example 9: Cationic Emulsions E6 of Carbamato-Functionalized Polydimethylsiloxane 2

An Ultra-Turrax T 50 emulsifying apparatus (from Janke & Kunkel/IKA) is initially charged with 22.0 g of isotridecyl pentaethoxylate, commercially available under the Lutensol TO 5 brand name (from BASF), 10.0 g of diethylene glycol monobutyl ether, commercially available under the Butyldiglycol trade name (from Brenntag), 1.50 g of N,N-bis[ethyl(tallowate)]-N-(2-hydroxyethyl)-N-methylammoniummethylsulfate (90% ethanolic solution), commercially available under the Stepantex® VK90 brand name (from Stepan) and 22.0 g of demineralized water. 66.0 g of the carbamato-functionalized product 2 are added in two portions under a high shear of 4000 to 6000 rpm, so as to result in a lotion-like preliminary emulsion. The emulsion is diluted with 77.58 g of demineralized water in portions under low shear to give the desired emulsion, to which are then finally added 0.5 g of 80% acetic acid and 0.40 g of sodium acetate. The result is a clear emulsion E6 having an average particle size of 21 nm. The emulsion is homogeneous and stable even after storage at room temperature for 6 months.

Example 10

Aqueous formulations F1-F3, F7 and F9 (inventive) comprising
(A) carbamato-functionalized polydiorganosiloxanes and
(B) cationic surfactants.
Aqueous formulation F4 (noninventive) comprising
(B) cationic surfactants without component (A).
Aqueous formulations F5 and F6 (noninventive) comprising
(A) carbamato-functionalized polydiorganosiloxanes without component (B).

The application tests for soft hand, droplet absorption time, easy ironing and crease repetition angle were effected using the following aqueous formulations described in table 1:

TABLE 1

Aqueous formulations F1 to F8

| | Emulsion of carbamato-functionalized polydimethylsiloxane | Cationic surfactant T1*** | Water | Electrolytes, perfumes, dyes, preservatives |
|---|---|---|---|---|
| F1*) | 2.1 g E2 | 2.1 g | 32.3 g | 0.7 g |
| F2*) | 2.1 g E3 | 2.1 g | 32.3 g | 0.7 g |
| F3*) | 1.1 g E1 | 2.3 g | 20.7 g | 0.5 g |
| F4**) | — | 3.5 g | 31.2 g | 0.3 g |
| F5**) | 17.6 g E2 | — | 19.5 g | 0.3 g |
| F6**) | 17.6 g E3 | — | 19.5 g | 0.3 g |
| F7*) | 2.1 g E4 | 2.1 g | 32.3 g | 0.7 g |
| F8*) | 2.1 g E5 | 2.1 g | 32.3 g | 0.7 g |

*)inventive
**)noninventive
***)T1: N,N-bis[ethyl(tallowate)]-N-(2-hydroxyethyl)-N-methylammonium methylsulfate (90% ethanolic solution), commercially available under the Stepantex ® VK90 trade name (from Stepan) (surfactant of the formula (B2-1))

The formulations (inventive and noninventive alike) are produced by heating the water to 50° C. The cationic surfactant which has been melted beforehand at 50° C. and stirred vigorously is added at this temperature with vigorous stirring (with the aid of a IKA Eurostar Power basic stirrer system with paddle stirrer). Stirring is continued until a homogeneous mixture results. The mixture is cooled to 30° C., and the emulsion of carbamato-functionalized polydimethylsiloxane and further ingredients are added.

Example 11

In an analogous manner to that described in example 10, rather than the cationic surfactant (T1) N,N-bis[ethyl(tallowate)]-N-(2-hydroxyethyl)-N-methylammonium methylsulfate, the following cationic surfactants were used:
cetyltrimethylammonium chloride (29% aqueous solution), commercially available under the Genamin CTAC name (from Clariant) (cationic surfactant T2) (surfactant of the formula (B1-1)),
N,N-distearyldimethylammonium chloride (95% strength), commercially available under the ARO-SURF® TA 100 brand name (from Evonik) (cationic surfactant T3)
(Surfactant of the formula (B1-2))
N,N-di(alkylcarboxyethyl)-N-hydroxyethyl-N-methyl-ammonium methylsulfate (alkyl=C16-alkyl, C18-alkyl, C18-alkylene) (86% ethanolic solution), commercially available under the brand name REWOQUAT® WE 45 (from Evonik) (cationic surfactant T4)(surfactant of the formula (B2-1))
1-methyl-2-talloylamidoethyl-2-talloylimidazolinium methylsulfate (90% solution in isopropanol), commercially available under the ACCOSOFT® 808-90 brand name (from Stepan) (cationic surfactant T5) (surfactant of the formula (B2-3))
1-methyl-2-norstearyl-3-stearamidoethylimidazolinium methosulfate (75% solution in isopropanol), commercially available under the REWOQUAT® W 75 brand name (from Evonik) (cationic surfactant T6) (surfactant of the formula (B2-3))
N,N-(talloylamidoethyl)-N-polyethoxyethyl-N-methyl-ammonium methosulfate (90% solution), commercially available under the Varisoft® 222 LM (90%) brand name (from Evonik) (cationic surfactant T7) (surfactant of the formula (B2-4))

The specified cationic surfactants T2 to T7, in the case of the noninventive formulations, were formulated as 10% formulations (based on the solids content) (F9 to F14) or, in the case of the inventive formulations, as 5% formulations (based on the solids content) together with 5% of emulsion E2 of carbamato-functionalized polydimethylsiloxane (F15 to F20). Formulations F9 to F14 and F15 to F20 are summarized in table 2.

TABLE 2

Aqueous formulations F9-F14 (noninventive) and F15-F20 (inventive)

| | Emulsion of carbamato-functionalized polydimethyl-siloxane | Cationic surfactant |
|---|---|---|
| F9**) | — | T2, 10% by wt. |
| F10**) | — | T3, 10% by wt. |
| F11**) | — | T4, 10% by wt. |
| F12**) | — | T5, 10% by wt. |
| F13**) | — | T6, 10% by wt. |
| F14**) | — | T7, 10% by wt. |
| F15*) | E2, 5% by wt. | T2, 5% by wt. |
| F16*) | E2, 5% by wt. | T3, 5% by wt. |
| F17*) | E2, 5% by wt. | T4, 5% by wt. |
| F18*) | E2, 5% by wt. | T5, 5% by wt. |
| F19*) | E2, 5% by wt. | T6, 5% by wt. |
| F20*) | E2, 5% by wt. | T7, 5% by wt. |

*)inventive
**)noninventive

Example 12: Use Examples

To assess the desired effects with regard to soft hand, droplet absorption time, easy ironing and crease recovery angle, all the modified textiles were washed together with about 2 kg of ballast material in a MIELE Softronic W 1935 WPS EcoLine domestic washing machine with the boil/colored wash program at 40° C. and spun at 1200 rpm. The washing surfactant dosed in was 65 g of an ECE-2 washing powder test laundry detergent from WFK. After the wash cycle, formulations F1 to F8 (pre-diluted in 1 liter of tap water with 16° dH) were added via the detergent drawer. Subsequently, two further wash cycles each of duration 90 minutes were conducted without intermediate drying. Finally, the material was dried on a line at 23° C. and 60% air humidity for at least 12 hours in a climate-controlled chamber.

Determination of Soft Hand (Hand Assessment):

Since the softness of textiles is highly subject to the subjective perception of testers, it is possible to achieve standardization of the boundary conditions only, and not of the assessment. In order nevertheless to assure reproducibility, the modified specimens were assessed with regard to their soft hand and arranged into a ranking. For this purpose, 10 testers awarded 1 to n marks depending on the number n of specimens tested, where n marks were awarded for the softest specimen and 1 mark for the specimen modified with the lowest softness. The unmodified reference specimen received 0 marks. The assessment of hand of a specimen is thus calculated as the average of the points apportioned to each specimen.

The soft hand results for formulations F1 to F8 are summarized in table 3.

TABLE 3

Assessment of soft hand
Assessment of soft hand on terry cloth (basis weight 500 g/m$^2$) after washing machine treatment and drying

| F1 (inventive) | +++ |
|---|---|
| F2 (inventive) | +++ |
| F3 (inventive) | ++ |
| F4 (noninventive) | + |
| F5 (noninventive) | o |
| F6 (noninventive) | o |

TABLE 3-continued

Assessment of soft hand
Assessment of soft hand on terry cloth (basis weight 500 g/m$^2$)
after washing machine treatment and drying

| F7 (inventive) | +++ |
|---|---|
| F8 (inventive) | +++ |

+++ excellent softness,
++ very soft,
+ soft,
o hard

The modification of the textile with formulation F4 has a soft hand; the textile seems greasy at the surface.

The modification of the textile with formulations F5 and F6 surprisingly has a hard hand on application in the washing machine.

The modification of the textile with formulations F1 to F3 and F7 or F8 leads to a natural, pleasant soft hand which, especially in the case of formulation F2 or F8, feels dry and voluminous at the surface, and in no case greasy.

The modification of the textile with a combination of carbamato-functionalized polydiorganosiloxanes and cationic surfactant surprisingly leads to distinctly better soft hand than the modification of the textile with a cationic surfactant or, in particular, the carbamato-functionalized polydiorganosiloxane alone.

In the case of finishing with the formulations of the invention, no yellowing of the textiles was found, which is surprising especially in the case of the formulations that contain emulsions of carbamato-functionalized polydimethylsiloxane 2 with a low degree of functionalization of the amino groups.

In an analogous manner, the soft hand of the inventive formulations F15 to F20 was compared with the soft hand of the noninventive formulations F9 to F14. An improvement in soft hand was likewise detected with the inventive formulations F15 to F20.

Droplet Absorption Time:

A droplet of deionized water was placed onto the stretched material surface of the modified textile after the washing machine treatment and drying from a height of 4 cm, and the time until the water droplets had been absorbed by the material was determined. Five determinations were conducted, and the average was formed.

The droplet absorption time results for the formulations of the invention as compared with the noninventive formulation are collated in table 4.

TABLE 4

Determination of droplet absorption time
Droplet absorption time on terry cloth (basis weight 500 g/m$^2$)
after washing machine treatment and drying

| F1 (inventive) | +++ |
|---|---|
| F2 (inventive) | +++ |
| F4 (noninventive) | + |

+++ 0-3 seconds,
++ 3-5 seconds,
+ 5-25 seconds

The modification of the textile with a combination of carbamato-functionalized polydiorganosiloxanes and cationic surfactant (F1 and F2, inventive) leads to a distinct reduction in droplet absorption time on knitted cotton fabric than modification with the cationic surfactant (F4, noninventive) alone. In the case of the textile, this achieves both improved softness and better water absorption than in the case of modification of the textile with formulations according to the prior art.

Easy Ironing

The finished textile that has been washed and dried (as specified above) is stretched over an oblique plane. The oblique plane has a length of 100 cm and an angle of inclination of 13.5°. A conventional Tefal electric iron is heated ("Cotton" position), placed onto the upper end of the plane and allowed to slide down the oblique plane. The time until it reaches the lower end of the oblique plane is measured. This procedure is repeated until a constant value is attained. The heat of the electric iron is reset before each procedure.

The easy ironing results for the inventive formulations compared to the noninventive formulation are summarized in table 5.

TABLE 5

Determination of easy ironing
Easy ironing on 100% cotton (basis weight 170 g/m$^2$) after
washing machine treatment and drying

| F1 (inventive) | 0.75 m/sec. |
|---|---|
| F2 (inventive) | 0.41 m/sec |
| F4 (noninventive) | 0.05 m/sec. |

The modification of the textile with formulation F1 or F2 by comparison with formulation F4 leads to a distinctly higher sliding speed, and hence a distinctly reduced application of force necessary for ironing of the textile.

Crease Recovery Angle

The determination is effected according to method DIN 53 890/1972 (where the exact description of the method can also be found):

Samples having a size of length 50 mm and width 20 mm are taken from the textile to be tested. Each sample is folded over in transverse direction, such that the length of the sample flank to be laid over is 10 mm. A metal foil of thickness 0.15 mm is placed under the sample flank to be laid over, in order to prevent adhesion of the fibers. The sample is covered with a microscope slide and weighted down with a weight of 1000 g such that the weight rests on the overlaid sample flank only. The load application time is 30 min.

After the weight on the microscope slide has been removed, the gradually increasing crease recovery angle after 5 and 30 min is determined with a protractor on either side of the angle flank.

At least 10 samples should be prepared and tested for each textile. The measurement results reported are the averages from the respective determinations.

The crease recovery angle results on cotton or on blend fabric for the formulations of the invention compared to the noninventive formulation are summarized in tables 6 and 7.

TABLE 6

Determination of crease recovery angle on cotton
Crease recovery angle on 100% cotton (basis weight 170 g/m$^2$)
after washing machine treatment and drying

|  | After 5 min | After 30 min |
|---|---|---|
| F1 (inventive) | 41° | 45° |
| F2 (inventive) | 37° | 43° |
| F4 (noninventive) | 21° | 33° |

TABLE 7

Determination of crease recovery angle on blend fabric
Crease recovery angle on blend fabric (basis weight: 125 g/m$^2$)
after washing machine treatment and drying

|  | After 5 min | After 30 min |
| --- | --- | --- |
| F2 (inventive) | 97° | 108° |
| F4 (noninventive) | 69° | 77° |

The modification of the textile with a combination of carbamato-functionalized polydiorganosiloxanes and cationic surfactant (F1 and F2, inventive) leads to a distinct increase in crease recovery angle in the case of knitted cotton material and in the case of blend fabric material compared to modification with the cationic surfactant (F4, noninventive) alone. In the textile, this achieves a distinct reduction in creasing tendency compared to that afforded by the prior art.

The invention claimed is:

1. An aqueous composition, comprising:
(A) at least 0.1% by weight and at most 10.0% by weight of at least one carbamato-functionalized organopolysiloxane comprising, on average, per molecule, at least one carbamato-functionalized group Y of the formula:

—R$^4$—[NX—R$^5$—]$_n$NX—H where
X is the same or different and is a hydrogen atom or a Z radical of the formula:

—CO—O—CHR$^6$—CH$_2$—OH or —CO—O—CH$_2$—CHR$^6$—OH wherein in the carbamato-functionalized organopolysiloxane (A), at least 5 mol % and less than 50 mol % of the N-bonded X radicals in the Y groups are not a hydrogen,
where on average at least one X radical per molecule is a Z radical,
where R$^4$ is the same or different and is a divalent, Si—C-bonded hydrocarbyl radical having 1 to 18 carbon atoms,
R$^5$ is the same or different and is a divalent hydrocarbyl radical having 1 to 6 carbon atoms,
R$^6$ is the same or different and is a hydrogen atom or a monovalent hydrocarbyl radical having 1 to 36 carbon atoms, where one or more —CH$_2$— groups may be replaced by a heteroatom,
n is 1, 2, 3 or 4,
(B) at least 1% by weight of one or more cationic surfactants, and
(C) at least 30% by weight and at most 97% by weight of water,
the weight percentages based in each case on the total weight of the aqueous composition.

2. The composition of claim 1, wherein at least one carbamato-functionalized organopolysiloxane (A) comprises a carbamato-functionalized polydiorganosiloxane of the formula

[R$^1$$_2$R$^2$SiO$_{1/2}$]$_2$[R$^2$(Y)SiO$_{2/2}$]$_k$[R$^1$$_2$SiO$_{2/2}$]$_m$   (I)

where
R$^1$ is the same or different and is a monovalent Si—C-bonded hydrocarbyl radical having 1 to 18 carbon atoms,
R$^2$ is the same or different and is a R$^1$ radical or a hydroxyl group —OH or alkoxy group of the formula —O—R$^3$ where R$^3$ is an optionally substituted alkyl radical having 1-8 carbon atoms, where on average at least one Y group per molecule contains a Z radical of the formula —CO—O—CHR$^6$—CH$_2$—OH or —CO—O—CH$_2$—CHR$^6$—OH, where
m is an integer and is at least 40 and at most 1000,
k is an integer and is at least 1 and at most 40,
where the ratio of m to k is at least 25 and at most 1000.

3. The composition of claim 1, wherein in the carbamato-functionalized organopolysiloxane (A), at least 15 mol % and less than 40 mol % of the N-bonded X radicals in the Y groups are not a hydrogen, but are defined as a Z radical of the formula:

—CO—O—CHR$^6$—CH$_2$—OH or —CO—O—CH$_2$—CHR$^6$—OH

4. The composition of claim 1, wherein R$^6$ is a methyl radical.

5. The composition of claim 1, the carbamato-functionalized organopolysiloxane(s) (A) are in the form of aqueous emulsions thereof comprising carbamato-functionalized organopolysiloxane (A), nonionic and/or cationic emulsifiers and water.

6. The composition of claim 1, wherein the cationic surfactants comprises:
(B1) quaternary ammonium surfactants of the formula

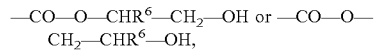   (B1)

where R is independently a hydrogen atom, an alkyl group, a hydroxyalkyl group, a benzyl group or a group of the formula —(C$_p$H$_{2p}$O)$_q$—H where p is an integer from 1 to 4 and q is an integer from 2 to 5, and
X$^-$ is a halide, a sulfate, a sulfonate, a nitrate, a methylsulfate or an ethylsulfate anion,
or
(B2) ester/amido-containing quaternary ammonium surfactants of the formula

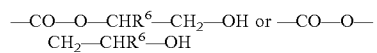   (B2)

where at least one R$^{20}$ radical is a monovalent hydrocarbyl radical containing a G group of the formula —O—(O)C—, —C(O)—O—, —NR—C(O)—, or —C(O)—NR— or

CR=NR, and the further R$^{20}$ radicals are independently an R group or a radical of the formula —R$^{20'}$—N+R$^{20}$$_3$ X$^-$
where R$^{20'}$ is an alkylene group,
the two ammonium groups R$^{20}$$_3$N+X$^-$ are joined to one another to form an R$^{20}$$_3$N-alkylene-NR$^{20}$$_3$ 2X$^-$ compound, or two R$^{20}$ radicals form an optionally unsaturated ring, and R and X$^-$ are as defined above.

7. The composition of claim 6, wherein the ester/amido-containing quaternary ammonium surfactants (B2) used comprise those selected from the group consisting of (B2-1) surfactants of the formula

(B2-1)

where

R$^{25}$ is independently a hydrogen atom, an alkyl group having 1 to 3 carbon atoms, a hydroxyalkyl group having 1 to 3 carbon atoms, a benzyl group or a group of the formula —(C$_p$H$_{2p}$O)$_q$—H where p is an integer from 1 to 4, preferably 2, and q is an integer from 2 to 5, R$^{26}$ is a monovalent hydrocarbyl radical, preferably an alkyl or alkenyl radical having 12 to 24 carbon atoms, R$^{27}$ is a divalent linear or branched alkylene radical having 1 to 6 carbon atoms, G$^1$ is a —O—(O)C—, —C(O)—O—, —NR—C(O)—, or —C(O)NR-group, r is 2 or 3 and X$^-$ is a halide, a sulfate, a sulfonate, a nitrate, a methylsulfate or an ethylsulfate anion, (B2-2) surfactants of the formula

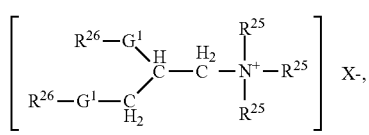
(B2-2)

where

R$^{25}$, R$^{26}$, G$^1$ and X$^-$ are as defined above, (B2-3) surfactants of the formula

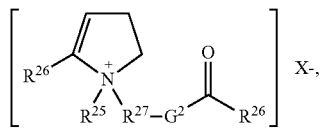
(B2-3)

where

G$^2$ is an oxygen atom or the NR$^{25}$ group,

R$^{25}$, R$^{26}$, R$^{27}$ and X$^-$ are as defined above, (B2-4) surfactants of the formula

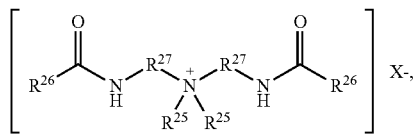
(B2-4)

where

R$^{25}$, R$^{26}$, R$^{27}$ and X$^-$ are as defined above, (B2-5) surfactants of the formula

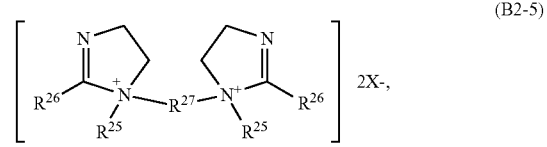
(B2-5)

where

R$^{25}$, R$^{26}$, R$^{27}$ and X$^-$ are as defined above, and mixtures thereof.

8. The composition of claim 1, wherein the carbamato-functionalized organopolysiloxanes (A) are prepared by reaction of amino-functionalized organopolysiloxanes (A') containing on average per molecule at least one Y' group of the formula

with cyclic carbonates of the formula

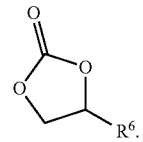

9. The composition of claim 8, wherein the amino-functionalized organopolysiloxanes (A') comprise amino-functionalized polydiorganosiloxanes (A') of the formula

[R$^1_2$R$^2$SiO$_{1/2}$]$_2$[R$^2$(Y')SiO$_{2/2}$]$_k$[R$^1_2$SiO$_{2/2}$]$_m$  (I')

where

R$^1$ is the same or different and is a monovalent Si—C-bonded hydrocarbyl radical having 1 to 18 carbon atoms, R$^2$ is the same or different and is an R$^1$ radical or a hydroxyl group —OH or an alkoxy group of the formula —O—R$^3$ where R$^3$ is an optionally substituted alkyl radical having 1-8 carbon atoms, where on average at least one Y group per molecule contains a Z radical of the formula —CO—O—CHR$^6$—CH$_2$—OH or —CO—O—CH$_2$—CHR$^6$—OH, where m is an integer and is at least 40 and at most 1000, k is an integer and is at least 1 and at most 40, and Y' group of the formula

10. The composition of claim 9, wherein the amino-functionalized organopolysiloxanes (A') have an amine value of at most 0.4 mmol/g.

11. The composition of claim 8, wherein the amino-functionalized organopolysiloxanes (A') have an amine value of at most 0.4 mmol/g.

12. A washing or cleaning composition comprising a composition of claim 1.

13. A method of fiber cleaning and/or care, comprising treating the fibers with a composition of claim 1.

14. A method of fiber cleaning or care comprising washing or cleaning the fibers with a composition of claim 12.

15. A cosmetic formulation comprising a composition of claim 1.

16. A method of hair care and washing, comprising contacting the hair with a composition of claim 1.

* * * * *

UNITED STATES PATENT AND TRADEMARK OFFICE
CERTIFICATE OF CORRECTION

PATENT NO. : 10,675,230 B2  
APPLICATION NO. : 16/096150  
DATED : June 9, 2020  
INVENTOR(S) : Christof Brehm et al.

Page 1 of 1

It is certified that error appears in the above-identified patent and that said Letters Patent is hereby corrected as shown below:

In the Claims

Column 26, Line 64, Claim 6:  
After "the two ammonium groups"  
Delete "$R^{20}{}_3N^+ X$" and  
Insert -- $R^{20}{}_3N^+ X$ --

Column 27, Line 5, Claim 7:  
Delete "$R^{25}{}_{(4-f)}(R^{26}\text{-}G^1\text{-}R^{27})_r N^+ X^- (B2\text{-}1)$" and  
Insert -- $R^{25}{}_{(4-r)}(R^{26}\text{-}G^1\text{-}R^{27})_r N^+ X^- (B2\text{-}1)$ --

Signed and Sealed this  
Sixth Day of October, 2020

Andrei Iancu  
*Director of the United States Patent and Trademark Office*